United States Patent
Castagna et al.

(10) Patent No.: US 11,806,160 B2
(45) Date of Patent: Nov. 7, 2023

(54) WEARABLE ELECTROCARDIOGRAPHIC MONITORING TECHNOLOGY (ECG) WITH AN AIRTIGHT CONTAINER FOR MEDICINES, AND INTEGRATED MEDICAL MONITORING SYSTEM

(71) Applicant: LÓTUS MEDICINA AVANÇADA, Belo Horizonte (BR)

(72) Inventors: Ilene Maria Guimaraes de Siqueira Castagna, Brumadinho (BR); Marco Tulio Vilaca Castagna, Belo Horizonte (BR)

(73) Assignee: LÓTUS MEDICINA AVANÇADA

( * ) Notice: Subject to any disclaimer, the term of this patent is extended or adjusted under 35 U.S.C. 154(b) by 939 days.

(21) Appl. No.: 16/347,777

(22) PCT Filed: Aug. 3, 2017

(86) PCT No.: PCT/BR2017/050219
§ 371 (c)(1),
(2) Date: May 6, 2019

(87) PCT Pub. No.: WO2018/081884
PCT Pub. Date: May 11, 2018

(65) Prior Publication Data
US 2019/0313968 A1    Oct. 17, 2019

(30) Foreign Application Priority Data

Nov. 7, 2016  (BR) .......................... 102016025939-8

(51) Int. Cl.
*A61B 5/00*   (2006.01)
*A41D 1/00*   (2018.01)
(Continued)

(52) U.S. Cl.
CPC ............ *A61B 5/4839* (2013.01); *A41D 1/005* (2013.01); *A41D 13/1245* (2013.01);
(Continued)

(58) Field of Classification Search
CPC ........... H04Q 2209/00; H04Q 2209/10; H04Q 2209/40; H04Q 2209/43; H04Q 2209/70;
(Continued)

(56) References Cited

U.S. PATENT DOCUMENTS 4,288,006 A * 9/1981 Clover, Jr. ........... B65D 47/265
                                                    222/42
6,304,797 B1   10/2001 Shusterman
(Continued)

FOREIGN PATENT DOCUMENTS

CN       102940488 A      2/2013
KR    2009-0123963 A      12/2009
(Continued)

OTHER PUBLICATIONS

Hsu et al., "Design of a Wearable 12-Lead Noncontact Electrocardiogram Monitoring System", Sensors, Mar. 28, 2019 (13 pages).
(Continued)

*Primary Examiner* — Franklin D Balseca
(74) *Attorney, Agent, or Firm* — Hamre, Schumann, Mueller & Larson, P.C.

(57) ABSTRACT

The present invention refers to a wearable, individual, customized and different sized technology for men and women, composed of electrodes, conductive track and airtight container for medicines, coupled to one another, and a mini electrocardiogram (ECG) apparatus containing a GSM (Global System Mobile) modem and a GPS (Global Positioning System) or a Bluetooth system which, through a wireless network specification within a personal scope (Wireless Personal Area Networks—PANs) deemed as
(Continued)

PAN-type or even WPAN, the electrical signal acquisition begins when the user press the button down. It is in the field of medical, recreational and/or sport applications, aiming at monitoring patients at high cardiovascular risk, being possible to diagnose it as soon as possible, aiming at shortening time to definite treatment of those who present acute coronary syndrome (ACS), acute myocardial infarction (AMI), acute atrial fibrillation-type (AAF) cardiac arrhythmias, and other cardiac arrhythmias or other cardiac pathologies capable to be detected by the electrocardiographic trace. Moreover the invention has tools to analyze a bunch of data—big data analytics and deeplearning—by utilizing artificial intelligence. Finally, the invention also has a module to proper administer the drug contained into the airtight container.

10 Claims, 5 Drawing Sheets

(51) Int. Cl.
| | | |
|---|---|---|
| | *A41D 13/12* | (2006.01) |
| | *A61J 7/04* | (2006.01) |
| | *B65D 83/04* | (2006.01) |
| | *A61B 5/282* | (2021.01) |
| | *A61J 1/03* | (2023.01) |
| | *G01S 19/13* | (2010.01) |
| | *H04Q 9/00* | (2006.01) |

(52) U.S. Cl.
CPC .......... *A41D 13/1281* (2013.01); *A61B 5/282* (2021.01); *A61B 5/6805* (2013.01); *A61B 5/7465* (2013.01); *A61J 7/04* (2013.01); *B65D 83/04* (2013.01); *A41D 2400/32* (2013.01); *A61B 5/0006* (2013.01); *A61B 2562/0209* (2013.01); *A61J 1/03* (2013.01); *G01S 19/13* (2013.01); *H04Q 9/00* (2013.01); *H04Q 2209/10* (2013.01); *H04Q 2209/40* (2013.01)

(58) Field of Classification Search
CPC .......... H04Q 2209/80; H04Q 2209/82; H04Q 2209/823; H04Q 2209/826; H04Q 2209/84; H04Q 9/00; A61B 5/4839; A61B 5/282; A61B 5/6805; A61B 5/7465; A61B 5/0006; A61B 5/0002; A61B 5/0004; A61B 5/0015; A61B 2562/0209; A41D 1/005; A41D 13/1245; A41D 2400/32; A41D 13/1281; A61J 7/04; A61J 1/03; B65D 83/04; G01S 19/13

See application file for complete search history.

(56) References Cited

U.S. PATENT DOCUMENTS

| | | | |
|---|---|---|---|
| 6,970,731 | B1 | 11/2005 | Jayaraman et al. |
| 7,412,281 | B2 | 8/2008 | Shen et al. |
| 9,282,893 | B2 * | 3/2016 | Longinotti-Buitoni ...................... A61B 5/6804 |
| 9,569,588 | B2 * | 2/2017 | Lowe ..................... G16H 10/65 |
| 9,569,592 | B2 * | 2/2017 | Heffron .................. A61B 50/10 |
| 9,662,030 | B2 * | 5/2017 | Thng .................... A61B 5/0059 |
| 10,123,741 | B2 * | 11/2018 | Wang ................... A61N 1/3987 |
| 2007/0219454 | A1 | 9/2007 | Guzzetta et al. |
| 2012/0158074 | A1 * | 6/2012 | Hall ..................... A61B 5/6804 607/5 |
| 2013/0254966 | A1 * | 10/2013 | Pattison ............. A41D 13/1245 2/69 |
| 2013/0281815 | A1 | 10/2013 | Varadan |
| 2014/0070957 | A1 | 3/2014 | Longinotti-Buitoni |
| 2014/0278475 | A1 | 9/2014 | Tran |
| 2014/0364779 | A1 | 12/2014 | Oestreich |
| 2015/0272464 | A1 | 10/2015 | Armoundas et al. |
| 2016/0066809 | A1 | 3/2016 | Chebiyyam |
| 2016/0095527 | A1 | 4/2016 | Thng et al. |
| 2016/0287480 | A1 * | 10/2016 | Hancock ................ G16H 20/13 |

FOREIGN PATENT DOCUMENTS

| | | |
|---|---|---|
| KR | 2010-0126107 A | 12/2010 |
| WO | 8902246 A1 | 3/1989 |
| WO | 2005/034743 A1 | 6/2006 |
| WO | 2008/116822 A2 | 10/2008 |
| WO | 2012088398 A2 | 6/2012 |
| WO | 2015/179015 A1 | 11/2015 |

OTHER PUBLICATIONS

Shao et al., "A Wearable Electrocardiogram Telemonitoring System for Atrial Fibrillation Detection", Sensors, Jan. 22, 2020 (16 pages).
Geng Yang et al., "A Health-IoT Platform Based on the Integration of Intelligent Packaging, Unobtrusive Bio-Sensor and Intelligent Medicine Box", IEEE Transactions on Industrial Informatics, pp. 2180-2191, Nov. 2014.
Upkar Varshney, "Wireless Medication Management System: Design and Performance Evaluation", Department of Computer Information Systems Georgia State University, 2011 (8 pages).

* cited by examiner

WEARABLE ELECTROCARDIOGRAPHIC MONITORING TECHNOLOGY (ECG) WITH AN AIRTIGHT CONTAINER FOR MEDICINES, AND INTEGRATED MEDICAL MONITORING SYSTEM

The present invention refers to a wearable technology, one-to-one, customizable and applicable in different sizes, and for men and women, composed of electrodes, an electronic circuit and an airtight container for medicines, coupled to one another, and a mini electrocardiogram (ECG) apparatus containing a GSM (Global System Mobile) modem and a GPS (Global Positioning System) or a Bluetooth system which, through a wireless network specification within a personal scope (Wireless Personal Area Networks—PANs), deemed as PAN-type or even WPAN, provides a way of connecting and exchanging information between the device with the embedded system and a mobile phone (smartphones) that use a specific application (app). The acquisition of electrical signals begins when a user presses down a button.

The present invention belongs to the field of medical applications, aiming at monitoring patients with high cardiovascular risk, being possible to present a diagnose as soon as possible, aiming for a reduced time to start a definite treatment of those who present acute coronary syndrome (ACS), acute myocardial infarction (AMI), acute atrial fibrillation-type (AAF) cardiac arrhythmias, and other cardiac arrhythmias or other cardiac pathologies detectable by electrocardiographic trace; as well as for recreational and/or sportive applications, aiming at monitoring individuals who desire their electrocardiographic trace to be followed up during their physical, recreational or sportive activities, being possible to evaluate their performance in a single or evolutionary manner, or even have their electrocardiogram recorded and written. The system analyzes the data—big data analytics and deep learning—by utilizing artificial intelligence, through the internet of things.

The ECG apparatus captures electronic signals through the electrodes, allowing a remote electrocardiogram monitoring. The data collected by the ECG vest and the location by the GPS are transferred online via GSM or Bluetooth to a user's mobile phone (smartphone), which has an app, and from this app to a datacenter having an Integrated Monitoring System (IMS) in a secure and reliable manner, with a 24×7×365 coverage. The GPS of the ECG apparatus, or of the smartphone itself in the case of transmission via Bluetooth to the smartphone, enables locating the individual who is wearing the electrocardiographic vest. The compartment for medicines is integrated to the electronic circuit of the ECG apparatus and is controlled remotely.

This wearable hardware- and software-integrating device allows the transmission of low voltage electronic signals through Internet of Things to the integrated monitoring center, as well as create an interface which enables to shorten responsive time from early symptoms, that may be a sign of an ACS, or an AMI, or an AAF, or another cardiac arrhythmia, to the definite treatment, which may also anticipate the beginning of treatment by remotely dispensing the medicines available in a plastic box of medicines coupled to the mini ECG.

The coronary artery disease (CAD) is the main cause of death worldwide. The acute myocardial infarction (AMI) is the complete occlusion of coronary artery, vessel that irrigates the cardiac muscle. The best option of treatment is the primary angioplasty, i.e., unclogging the coronary artery through balloon catheter. The earlier the coronary opening, the better the treatment result, reducing the morbidity and mortality rates. The maximum optimal delay between an entry of an individual to an emergency (door) and a diagnose and treatment is up to 90 min. The main metric in the treatment of AMI is Door to Balloon time: "D2B", which is the time from patient arrival at emergency to his or her coronary opening by primary angioplasty with a balloon catheter or stent.

There is a need for the patient to have more autonomy, information and the possibility of using resources such as telehealth to obtain analyses, diagnoses and even start treatment regardless of their location. Through constant technological advance and the facilities of computing and mobile communication, it is proposed to expand the limits of this D2B paradigm in the AMI, ACS and in the AAF approach and other cardiac arrhythmias.

All data generated by the technology coupled to the vest claimed in the present invention are triangulated by the monitoring center, the hospital network and a specialist medical professional. Through an electronic signal sent by the monitoring center, the doctor responsible for the electrocardiographic trace analysis provides the diagnose and, if necessary, triggers remotely the opening of the medicines compartment, thus initiating the treatment in advance and also reducing the time from the initial symptom of the patient with coronary obstruction to the moment of effective and definite treatment, which is the coronary artery opening by primary angioplasty. The same process may be carried out regarding cardiac arrhythmia, such as AAF, with less than 24 to 48 hours of onset of symptoms, providing definite treatment with the dispensing of appropriate medicine by remotely opening the compartment with medicines as soon as a diagnosis is made.

Individuals having CAD are instructed to self-monitor with the support of telemedicine to expedite the identification of their symptoms. Thus, the significant reduction in time from symptom onset to coronary opening will occur through the combination of a remote monitoring network that generates reports and supports patients at risk of AMI and ACS, popularizing the use of the wearable device. The same can happen with patients presenting AAF-type arrhythmia, from the moment they feel changes in cardiac heart rhythm starting within a period of up to 48 hours.

The development of wearable technologies and Internet of Things provide several possibilities of application in healthcare, such as remote monitoring of individuals at cardiovascular risk and the elderly. With the available technology, in addition to prevention programs through educational initiatives, there are opportunities to provide healthcare.

Data collected by an ECG vest and its location by a GPS (Global Positioning System) are transferred online via GSM (Global System Mobile) or via Bluetooth, coupled to the electrocardiogram device, to a smartphone containing an app, and from there to a datacenter with an Integrated Monitoring System (IMS). The IMS will assign the received ECG data to a doctor who will promptly issue an ECG report electronically.

The IMS will have previously registered a hospital network and the medical professionals able to issue the reports of monitored patients. Once AMI or ACS is identified, the team that works in the IMS will assist the patient, indicating first procedures and will forward names and addresses of hospitals closest to the patient that are suitable for care. If AAF or other cardiac arrhythmias have been identified by the accredited doctor, the patient will be instructed to take the specific medication for this pathology, after the remote opening by electronic signal of the plastic box containing the appropriate medicine.

Some documents that present technologies on clothes with coupled ECG or GSM technology or GPS or Bluetooth were identified, without, however, the specified functionality of using a complex monitoring system integrated with the patient, as well as access to the airtight plastic box containing medicines for emergency care with remote opening through an encrypted digital signature by the doctor.

The document "Elastic garment for positioning and fixing ECG electrodes" (US20160066809) describes only a garment with markings for positioning and attaching electrodes and does not describe a fabric that provides elastic tensile on the body such that the electrodes are close to the skin. They are composed of horizontal and vertical embroidery of stainless-steel yarns, crossing each other on the fabric of the garment, alone or associated with silver- or carbon-based dyes or pastes, or conductive stretchable textiles, in order to form a mesh to increase the contact surface with the underlying skin. It does not refer to any device that contains an airtight container for medicines that allow remote dispensing of medicines in case of specific needs such as ACS, AMI, AAF and other cardiac arrhythmias, for early treatment of these pathologies.

The document "Wearable remote electrophysiological monitoring system" (US201302818150) consists of an electrophysiological monitoring system that record ECG data of the ECG that is attached to a garment. It presents a wireless transmitter and a controller configured to collect data generated by the ECG and transmit to a receiver, and in the case of any abnormality, it issues am alert. The document "Multi-layered sensor apparatus" (WO2012088398) describes only a cloth formed by an array of interconnected sensor, without, however, demonstrating that these sensors are part of an ECG device for continuous or intermittent monitoring, and none of the documents describes the remote monitoring functionality of the ECG in real time, and also does not refer to any device that contains an airtight container for medicines that allow remote dispensing of medicines.

The document "Wearable medical treatment device" (EP2590710) refers to a wearable technology that includes a cardiac detection electrode, a treatment electrode, a user interface configured to receive information, and a sensor configured to detect some abnormal physiological activity. But it does not show a complete ECG device, nor does it refer to any type of intermittent monitoring integrated into any system, remote or not. It does not refer to any remote control device for opening an airtight plastic box containing appropriate medicines for starting the emergency care through an encrypted digital signature.

The document "ECG method and system for optimal cardiac disease detection" (US20070219454) describes a method of indicating heart disease through electrocardiogram signals from a set of electrodes fixed to the patient's body for detection and mapping of heart diseases in the individual's body, and the document "Wireless transmitted electrocardiogram monitoring device" (U.S. Pat. No. 7,412, 281) only references a wireless electrocardiogram monitoring system for long-term physical status monitoring. None of the documents make reference to a wearable technology with complex functionalities of mapping and transmitting remote data to a monitoring center, as well as access to the treatment of heart disease, when applicable, by opening the airtight plastic box containing medicines as previously described.

The documents "Apparatus for, and method of, determining the condition of a patient's heart" (EP1673010) and "Ambulatory physiological evaluation system including cardiac monitoring" (WO8902246) describe a vest adapted to be worn on the patient upper body and an ambulatory evaluation system to monitor the cardiac activities of a patient, but do not comprise the complete system of integrated intermittent monitoring and remote reading of patient data with the possibility of prompt care and prompt treatment.

In turn, the document "Independent non-interfering wearable health monitoring and alert system" (CA2839954) describes a cloth with a system that includes a multi-ECG measurement device with alert markers from changes and health anomaly detections, being that the yellow alert level serves as an indicator to seek medical check-up, and the red alert level serves as an alert to seek immediate medical help. However, they do not have the specific functionality of using a complex monitoring system integrated with the patient, in which alerts are sent to a specific center that trigger a complete remote care, identifying the place of care by the apparatus GPS coupled to the cloth; then the doctor in charge, by remote access and encrypted digital signature, will open an airtight plastic box containing medicines for immediate start of treatment until the arrival of an ambulance and care at the hospital or other suitable place.

None of the documents found in the state of art mentions or alludes to technology that is similar or that presents performance, efficiency and integration of equipments similar to those of the present invention, as well as complex functionalities of mapping and transmission of remote data to a monitoring center, use of artificial intelligence, "deep learning" and big data analytics, as well as access to early initiation of treatment for coronary artery disease, whether AMI or ACS, AAF, with less than 48 hours of onset or other cardiac arrhythmias, when applicable, through the opening of the airtight plastic box containing medicines as described above, by remote transmission of an electronic signal, authorized and carried out by the doctor who reports the ECG.

SUMMARY OF THE INVENTION

The present system comprises a wearable electrocardiographic (ECG) monitoring system with an airtight compartment for medicines and an integrated medical monitoring system consisting of wearable technology that is washable, for medical, recreational and/or sportive applications. The system is composed of electrodes and an electronic circuit composed by a conductive track and hardware, and the airtight compartment. The above items are coupled to each other and to a mini-ECG device containing a GSM (Global System Mobile) modem and a GPS (Global Positioning System) or a Bluetooth (BLE) system for connection and exchange of an information between the integrated devices to a datacenter and a remote monitoring center. In addition, the acquisition of an electrical signals by the ECG starts automatically when a user presses down a button in a box containing the ECG device.

The airtight compartment is coupled to the electronic circuit of the ECG apparatus with GSM, GPS or BLE, and is controlled by a solenoid of an electromechanical system. Thus, an expert doctor, with an encrypted digital signature, can remotely trigger an opening of doors of the airtight compartment containing medicines for proper dispensing, after the confirmation of the diagnosis.

The remote monitoring of the electrocardiogram has the optional function of automatic interpretation of the trace to be carried out by ECG analysis software, supported by the expert doctor and an expert system, a software of Integrated Monitoring System online and a software integrated to a smartphone receiving the electronic signals that enable:

the electronic signals captured by the electrocardiogram to transmit the trace to the smartphone, displaying the trace in the smartphone in real time, via BLE transmission coupled to the electrocardiogram for that smartphone; and a recording of that tracing to be made for a period of 24 hours.

In addition, on-screen technology allows for self-monitoring of symptoms by patients, who can have their treatment initiated as soon as the symptom starts, and their ECG is remotely done.

The application-based communication of screen technology takes place as follows:

the user accesses a data via the smartphone, by GSM or BLE, in real time via the application, in addition to access a hardware with encompassed software, which performs the acquisition of the electrocardiographic signals;

the hardware with encompassed software has direct communication with the smartphone;

the smartphone communicates via Wi-Fi, 3G, 4G or 5G transmission with the integrated monitoring center and a second smartphone;

the second smartphone is accessed by the doctor or expert.

the integrated monitoring center communicates with the hospital or similar care center and with the doctor or expert via the second smartphone or a computer.

In addition, the vest of the wearable technology is comprised by a polyamide textile yarn fabric or any fabric similar to synthetic and expandable rubbers that:

provides skin protection against the harmful effects of the sun;

offers bacteriostatic action, avoiding body odor;

is biodegradable.

enables the electrodes to have stainless steel yarns horizontally and vertically embroidered by crossing or meshing one another on the cloth, so as to form a mesh to widen the surface contacting the underlying skin, in a rectangular or square shape, with conductivity property of electronic signals; or composed of silver- or carbon-based pastes or dyes or stretchable conductive fabrics, in a single manner or associated to the mesh of stainless steel yarns, singly or associated to a silver- or carbon-based dye or pastes or stretchable conductive fabrics, as well as for printing low voltage electronic circuits over elastic films and fabric substrates; and contains stretchable encapsulating which is used to protect the low voltage circuit printed over the elastic film and substrate fabric.

The data collected by the ECG system and a location collected by the GPS are transferred online via GSM or by integrating BLE to the smartphone that contains an application (app), to the datacenter with an Integrated Monitoring System (SMI). Thus, said ISM will assign the received ECG data to a professional who will immediately and remotely provide an ECG report to the user, indicating the first procedures, allowing immediate interaction with an emergency hospital medical service and forwarding the names and addresses of nearby hospitals able perform urgent care.

The data storage is carried out by an electronic circuit U3 that includes a non-volatile memory, that is responsible for recording the acquired data for later transmission, and a circuit U8, that is composed by a solid-state relay responsible for the activation of an electromagnet to release the medicines from the compartment. In addition, there is an application request through an USB input for protection against outbreaks and electrostatic discharges, formed by an U7 circuit, a solid state TVS protector.

The said device that acquires the electrocardiographic signal is capable of acquiring 256 points per second and presents variation of the electric potentials generated by the electrical activity of the heart, which allows the reading of 8 channels and another 4 by means of mathematical calculations, being a 12-lead ECG, in at most 24 hours, and 8 seconds to adjust the impedance of each type of skin.

There is an application (app) installed on the smartphone to add a timestamp and the acquired GPS coordinate, and submit the examination to the FTP server, in addition to be able to display both a recorded exam and a real time monitoring of the cardiac signals; the file being not successfully sent, an error log is stored and a new attempt will be made, and this will be repeated until the exam is successfully submitted to the server and, then, is sent to the datacenter along with the next valid exam.

The on-screen hardware is powered by a rechargeable LI-ION battery containing LEDs and a buzzer to notify the patient a stage of an examination process and a battery status and has the Bluetooth module with an antenna for programming and setting up the device.

The on-screen system also enables the electrodes to be fixed directly on the skin of the patient and be arranged according to the EASI ECG system.

BRIEF DESCRIPTION OF FIGURES

For better understanding on how the "WEARABLE TECHNOLOGY OF ELECTIOCARDIOGRAPHIC (ECG) MONITORING WITH AIRTIGHT CONTAINER FOR MEDICINES AND INTEGRATED MEDICAL MONITORING SYSTEM", herein claimed, is constituted, the appended drawings are presented, wherein:

DETAILED DESCRIPTION OF THE TECHNOLOGY

Description of the Cloth Quality

Figure 1:
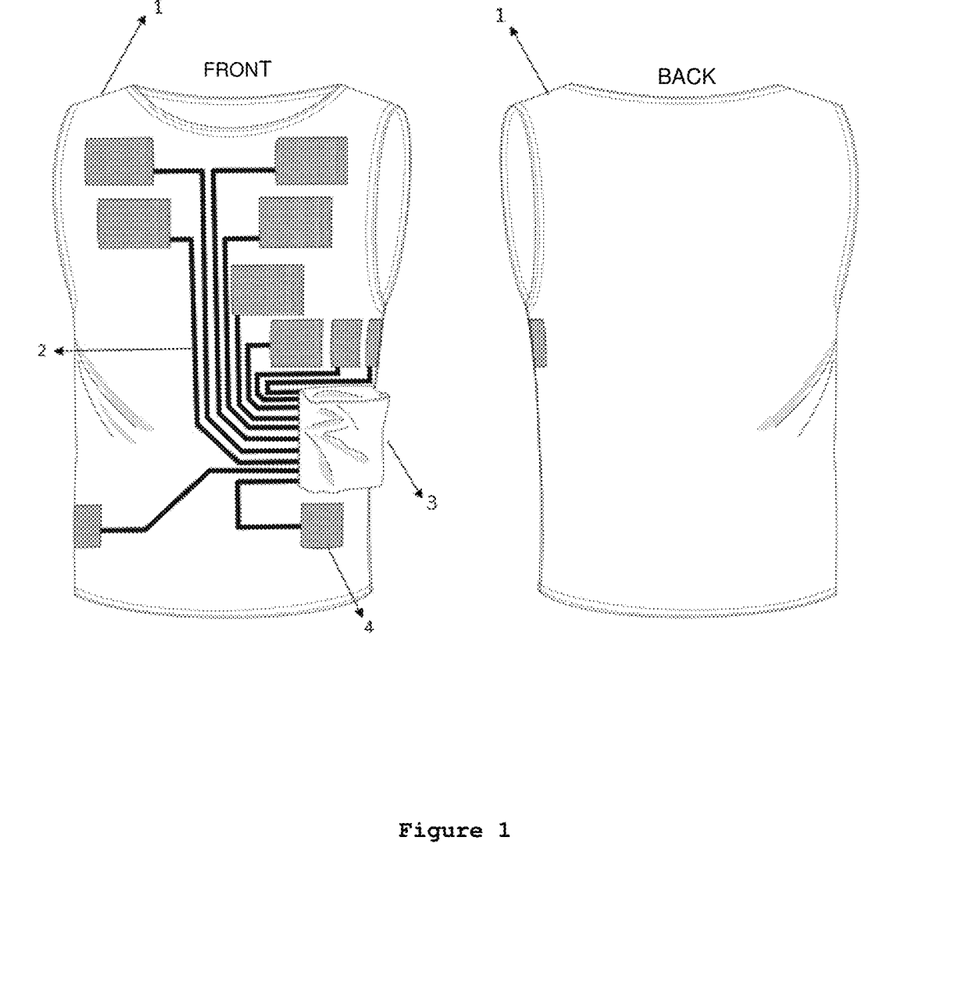
FIG. 1—wearable one-to-one, customizable and applicable in different sizes technology, for men and women, composed of a conductive track, an airtight container for medicines and electrodes, coupled to one another, and an electrocardiogram (ECG) apparatus.

A vest (1) is composed of a fabric of polyamide textile yarns 6.6, providing great comfort, lightness, softness, ease of care and functionality. Specifically, it is made of yarn that can i) offer protection to a user's skin against harmful effects of sunlight, ii) have a bacteriostatic action, preventing body odor, iii) be biodegradable, which allows clothes made therefrom to decompose in less than 3 years when properly disposed of in landfills.

These fabrics provide a tensile strength on the user's body in such a way that electrodes (4) are close and well-adjusted to the skin. The cloth electrodes (4) are connected to a conductive track (2) composed of horizontal and vertical embroidery of stainless steel yarns crossing each other on the cloth fabric, in a single manner or associated to silver- and/or carbon-based dye or paste or fabric, so as to form a mesh to widen the surface contacting the underlying skin in a rectangle or square shape about 5×5 cm$^2$ or 5×4 cm$^2$ or 4×4 cm$^2$ or 5×6 cm$^2$ or 6×6 cm$^2$ or 6×5 cm$^2$ or 6×4 cm$^2$. The electrodes (4) of the cloth composed of a stainless-steel embroidery in a single manner or associated to a silver- and/or carbon-based dye or paste or fabric has a property of conducting electrical signals. The "track" that conducts the electrical signal captured by the embroidered electrodes (4) and the conductive track (2) in contact with the user's skin consists of several lines resulting from the embroidery of stainless-steel wires associated or not with silver- and/or carbon-based dye or paste or carbon and/or silver fabric that conducts the electrical signal from the embroidered electrode to the connection with the electrocardiographic device. The electrodes (4) of the vest are composed of stretchable conductive pastes, dyes or fabrics of silver- and/or carbon, for printing low voltage electrical circuits on elastic films and textile substrates, having excellent distensibility, adhesion and conductance. These conductive textiles, dyes or pastes contain an encapsulating stretchable component which is used to protect the low voltage circuit printed onto the elastic film and substrate fabric as it has an excellent thin and extensible protection, adhesion and abrasion resistance. This system may be designed for wearable electronics applications that may require repeated washing.

The device encompasses the variation of electric potentials generated by electrical activity of the heart. 8 channels are read-out, and other 4 channels are generated by means of mathematical calculations. The acquisition of electrical signals starts when the patient presses down the button, 256 points per second being acquired during a span of 15 seconds, and about 8 seconds are required to set the impedance of each skin type. The read-out values are stored in a NOR memory until they can be sent to a server by means of a GPRS connection. Meanwhile, the GPS starts to synchronize satellites and identify the patient location until coordinates are received or the time limit is reached.

The wearable ECG monitoring technology (1) is a one-to-one customizable, adjusted to different sizes, and for men and women, in addition to be composed of a hardware, having 12 bypasses and an encompassed software with a feature of GPS access with interface for SIM card for GSM communication or through Bluetooth coupled to the ECG. This system will transmit the electronic signal of the ECG to an Analysis Software Module, generating graphics, thus allowing for a remote electrocardiogram monitoring, with optional function of automatic interpretation, coupled to a high technology of analysis of a bunch of data and utilizing artificial intelligence, big data analytics and deep learning. All data generated by the technology coupled to the cloth claimed in the present invention are based on monitoring center, hospital network and expert doctor.

The capture of the electronic signals by the electrodes allows for a remote monitoring of electrocardiogram, with optional function of automatic interpretation, supported by an expert system, a software of Integrated Monitoring System online that has interfaces with doctors, hospitals and clients integrating with SMS Broker.

After reading out the signals, the exam is sent to the server along with the coordinates of the location where the device was at the time of signal submission. If the file is not successfully sent, an error log is stored, and a new attempt is made after a certain amount of time, this is repeated until the exam can be submitted to the server. The log will be sent to the remote monitoring center along with the next valid exam. The equipment contains two LEDs and a buzzer to notify the patient of the stage of the exam.

The data collected by the ECG vest and its location by the GPS will be transferred online via GSM or via Bluetooth to the smartphone and from this one to a datacenter with an Integrated Monitoring System (IMS) having a safe and reliable 24×7×365 coverage. This IMS will assign the received ECG data to a doctor who will immediately provide the ECG report in an electronic manner.

Figure 2:
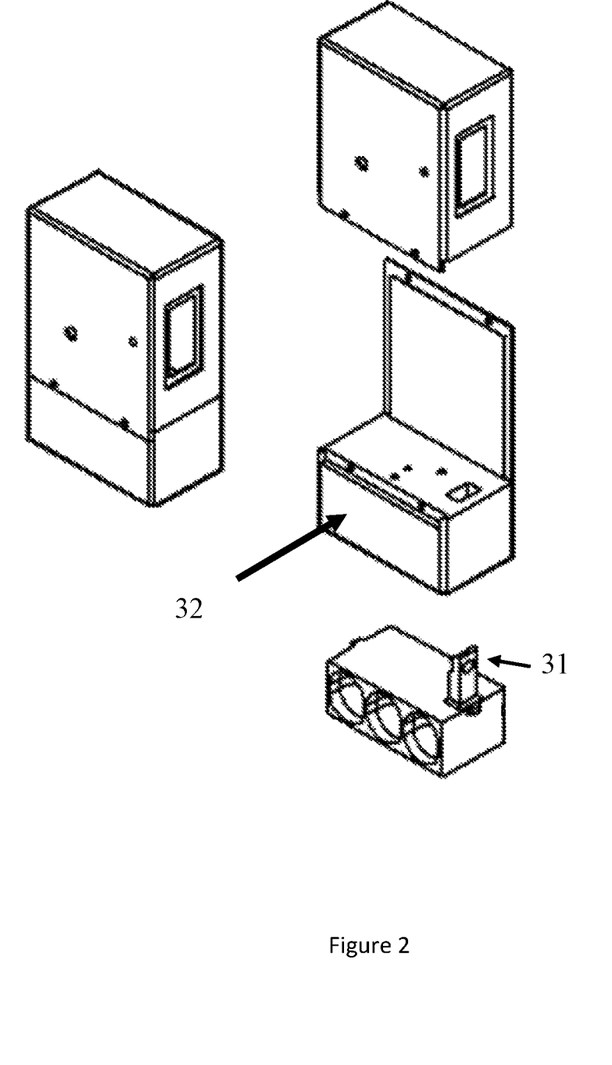
FIG. 2—airtight container for medicines, the lower compartment for fitting electronic pieces, the upper compartment for fitting electronic pieces, and a compartment for medicines.
Figure 3:
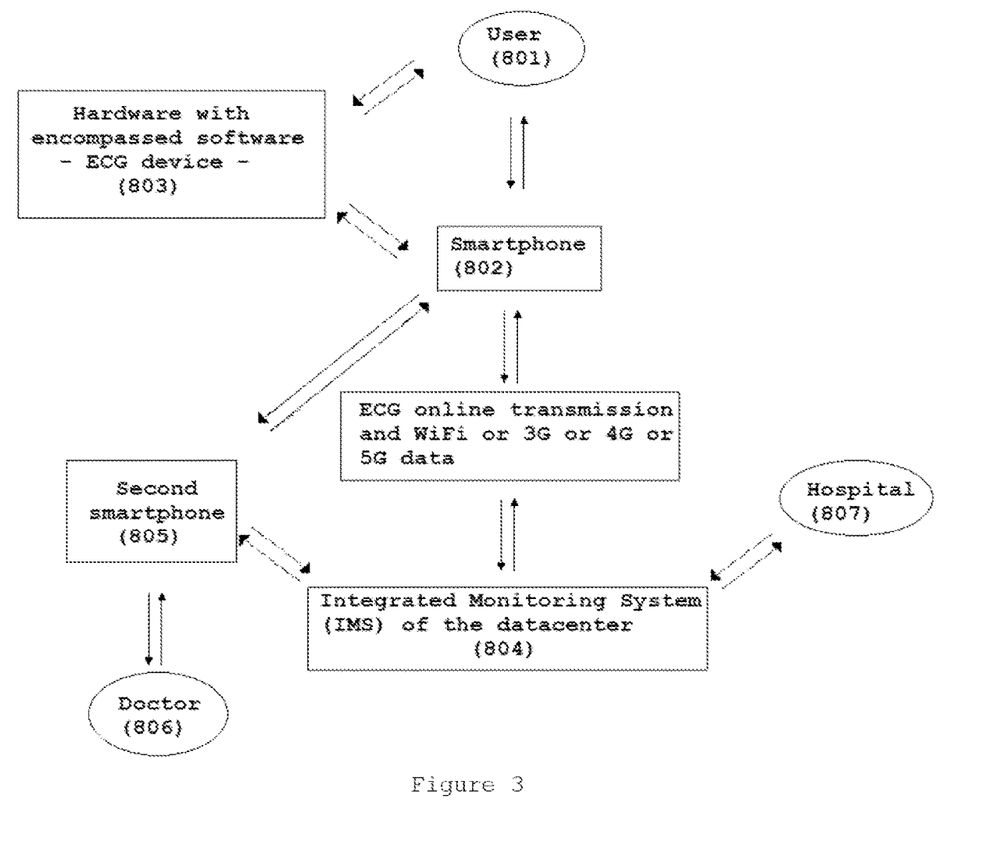
FIG. 3—communication system of the on-screen technology.
Figure 5:
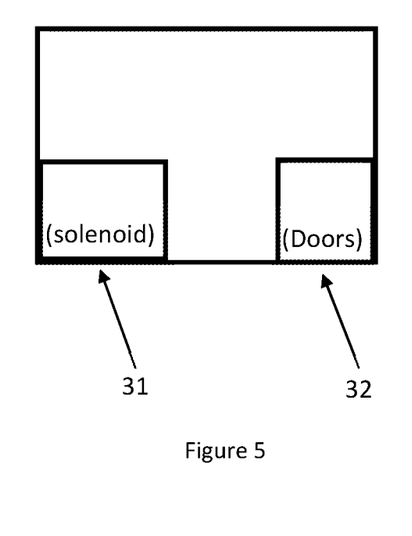

An airtight compartment (3) is attached to the device. The airtight compartment (3) contains specific medicines which are essential at the immediate start of the treatment of pathologies, such as ACS, AMI, AAF and other cardiac arrhythmias, is integrated to the electronic circuit of the ECG apparatus and controlled by a solenoid (31). The patient, victim of ACS, AMI, FAA and other cardiac arrhythmias, may get the treatment started as soon as the symptom starts, and his ECG is remotely done by self-monitoring.

The expert doctor, through an encrypted digital signature, will remotely trigger the opening of the compartment doors (32) containing medicines for proper remote dispensing, according to the diagnosis of the electrocardiographic trace. The server will identify the problem during the analysis, and remotely release access to the drug. The patient will receive a call informing that the drug has been released and then, can press the button down for 5 seconds. The device, on the other hand, finds out the release file on the server and releases access to the medicine so it can be ingested. The server will have in its database all contacts of registered clients and doctors.

Functional Description of the Circuit

Analog Front-End

The biometric (analog) data are read-out through the input connector J1, the signals pass through a high frequency filter formed by the components: R9, R5, R7, R11, R13, R15, R17, R19, R21, R25, R26, R22, R20, R18, R16, R14, R12, R8, R6, R23, C51, C52, C23, C24, C25, C26, C28, C29, C32, C33, C34, C35, C36, C37, C38, C3, C49, C50, C54, and C55.

The protection against electrostatic discharges at the input of the signals is made by the diodes D1 to D9, responsible for keeping the receiving levels within levels accepted by the A/D converter. Signal acquisition is performed by the U4 analog front-end, which consists of 8 24-bit delta-sigma A/D converters. The +2.5-Volt and −2.5-Volt symmetric voltage levels, required for the analog front-end signal levels to be suitable, are generated by the electronic circuits U1, U2 e U3.

Gps Coordinate Acquisition Module, Signaling and Triggering Button

Figure 4:
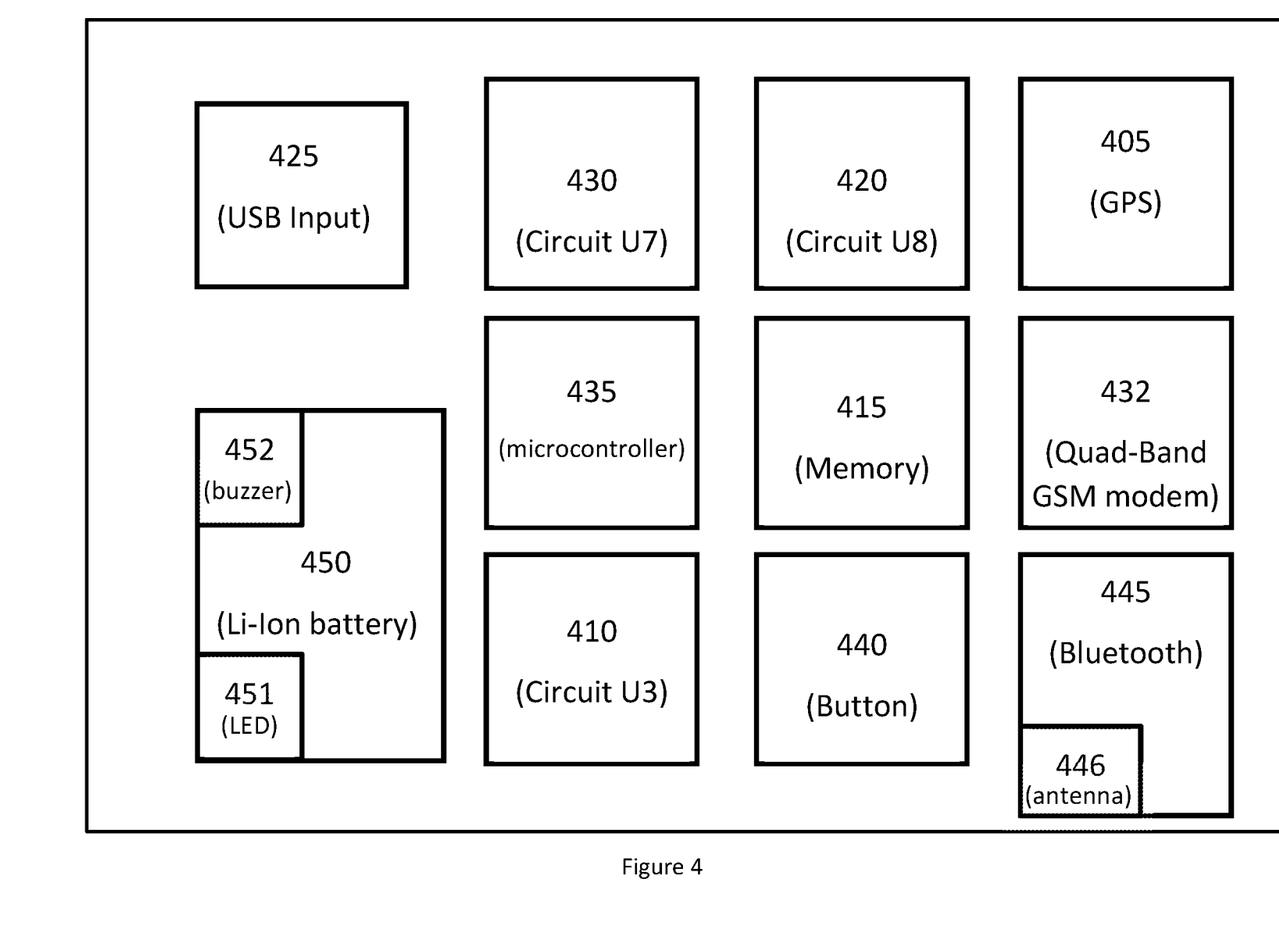
FIG. 4—upper view of the hardware containing the ECG and the electronic components, highlighting GPS, BLE, communication antenna, USB Input FIG. 5—upper view of the airtight container for medicines with a solenoid for opening of doors.

FIG. 4 illustrates the hardware containing the ECG and the electronic components.

For the acquisition of geographical coordinate data, a GPS module (405) formed by electronic circuit U1 is used, delivering data to the processing unit in the NMEA 0183 format, having latitude and longitude data. The LED1 and LED2 components are responsible for the operational signaling of the equipment and the key S1 to start operating.

Processing Unit and Gprs Module

The circuit is powered by a rechargeable LI-ION battery (450) whose management is the responsibility of the U1 electronic circuit, front-end dedicated battery charger. The electronic circuit U2 regulates the voltage levels to +3.3 V required for the operation of the other electronic circuits.

Data storage is performed by the electronic circuit U3 (410), and a non-volatile memory (415) is responsible for recording acquired data for later transmission. The circuit U8 (420) is composed of a solid-state relay responsible for the electromagnetic triggering in order to release the compartment for medicines, according to the application request. In case of an USB input (425), there is a protection against outbreaks and electrostatic discharges formed by the circuit U7 (430), a solid-state TVS protection.

The communication via GPRS is carried out by the electronic circuit U6, Quad-Band GSM modem (432), responsible for sending data to the FTP server. The circuit U5 is composed of a solid-state relay, responsible for disconnecting the GPRS Modem when it is not operating.

The connector J6 is a receptacle for GSM SIMCARD which has its own protection against electrostatic outbreaks carried out by the electronic circuit TVS1. The data processing and treatment are responsibility of the electronic circuit U4, a microcontroller (435) of the ARM family, responsible for executing the application software.

Integration of Mini Ecg-Bluetooth and Smartphone

The device acquires the variation of electrical potentials generated by the electrical activity of the heart. 8 channels are read out, and other 4 channels are generated by means of mathematical calculations. The electrical signals acquisition starts when the user presses down the button (440). 256 points per second are acquired, in a maximum of 24 h. Also, it takes about 8 seconds to set the impedance of each type of skin. The read-out values are stored in a NOR memory until they are sent to a smartphone via Bluetooth communication. There is an application installed on the smartphone to add the timestamp and the acquired GPS coordinate and submit the exam to the FTP server. It is possible both to see the recorded exam and monitor cardiac signals in real time. If the file is not successfully sent, an error log is stored, and a new attempt is made after a certain amount of time, this process is repeated until the exam is submitted to the server. The log is sent to the server along with the next valid exam. The hardware is powered by a rechargeable battery of LI-ION (450) and also contains three LEDs (451) and a buzzer (452) to notice the individual on the stage of the exam process and the battery status, a Bluetooth module 4.1 (445) with an antenna (446), and an USB input (425) for programming and configuring the equipment.

The present invention, among all the technological benefits described above, contributes to the immediate diagnosis of symptoms in ACS, AMI, AAF and other cardiac arrhythmias, and allows to dramatically reduce the time between onset of symptoms and the primary angioplasty, definitive treatment of AMI, early initiation of treatment in ACS and AMI and definitive treatment of AAF and other cardiac arrhythmias by proper administration of the drug contained in the airtight compartment (3). The medical and hospital network will have access to the IMS to update data, register new care teams and obtain patient information that is directed to their service. This allows for a reduced bureaucracy, more agility and avoids time loss in attending to these cardiovascular emergencies, considering that time is a prime factor in reducing the aggravation of these pathologies, especially when undiagnosed or delayed at the beginning of treatment.

The invention claimed is:

1. An electrocardiographic (ECG) monitoring system comprising:
    an airtight container for medicines, the airtight container including compartments each of which contains medicine; and
    an integrated medical monitoring system,
    wherein the ECG monitoring system comprises a wearable technology composed by the airtight container and the integrated medical monitoring system, the integrated medical monitoring system comprising a mini-ECG apparatus contained in a box, electrodes, and an electronic circuit comprising a conductive track and hardware with an encompassed software,
    wherein the hardware and the mini-ECG apparatus are contained within the box, the mini-ECG apparatus being configured to perform ECG analysis remotely and wherein acquisition of ECG electrical signals is started automatically when a user presses down a button on the box containing the mini-ECG apparatus,
    the ECG monitoring system configured for automated interpretation of a trace of the ECG electrical signals, wherein the interpretation of the trace is performed by an ECG analysis software and supported by a doctor or an expert, by the ECG analysis software with deep learning and data analytics in an integrated monitoring system (IMS) in a datacenter, and by a software integrated on a smartphone receiving the ECG electrical signals from the mini-ECG apparatus, which enables:
        the mini-ECG apparatus to transmit the trace of the ECG electrical signals to the smartphone via Bluetooth (BLE) transmission to be visible on the smartphone in real time through the software integrated on the smartphone, and
        a recording of the trace to be done over a period of 24 hours; and
    the hardware comprises:
        a GPS (Global Positioning System), and
        a system for connection and exchange of information comprising a GSM (Global System Mobile) modem and a Bluetooth (BLE) device,
    wherein the electrodes and the airtight container are coupled to one another via the conductive track of the electronic circuit,
    the system for connection and exchange of information is configured to exchange information with the datacenter, and the information exchanged with the datacenter is processed by the IMS with the deep learning and the data analytics ECG analysis software within the datacenter; and
    wherein the airtight container is controlled by a solenoid in an electromechanical system through which the doctor or the expert, with an encrypted digital signature, is able to remotely trigger dispensing of the medicines.

2. The ECG monitoring system, according to claim 1, characterized in that communication via the software integrated on the smartphone takes place as follows:
    the user accesses via the smartphone, by the GSM modem or the BLE device, data provided in real time via the software integrated on the smartphone, and accesses the mini-ECG apparatus, which performs the acquisition of the ECG electrical signals;
    the hardware has direct communication with the smartphone;

the smartphone communicates via wi-fi, 3G, 4G or 5G transmission with the IMS and with a second smartphone;

the second smartphone is accessed by the doctor or the expert; and the IMS within the datacenter communicates with a hospital or a similar treatment center and with the doctor or the expert via the second smartphone or a computer.

3. The ECG monitoring system, according to the claim 1, characterized in that the wearable technology is a wearable vest composed of a fabric of poly-amide textile yarns or any other fabric similar to synthetic or expansible rubber, the electrodes form a mesh of stainless steel yarns horizontally and vertically embroidered by crossing or meshing one another on the fabric, in a rectangular or square shape, wherein the wearable vest is configured to be conductive by being composed of silver-based or carbon-based pastes or dyes or stretchable conductive fabrics, and wherein the mesh of electrodes contains stretchable encapsulation to protect low voltage circuits printed over elastic films and fabric substrates.

4. The ECG monitoring system according to claim 3, characterized in that the mesh of the electrodes is in contact with a skin of the user.

5. The ECG monitoring system according to claim 1, characterized in that data collected by the mini-ECG apparatus and a location provided by the GPS are transferred online to the IMS within the datacenter, via the GSM modem or by integrating the BLE device with the smartphone, wherein the IMS assigns received ECG electrical signal data to the doctor or the expert, the doctor or the expert provides remotely to the user an electronic ECG report, indicates first procedures and forwards names and addresses of nearby specialized hospitals to the user, allowing for an immediate interaction with an emergency hospital service.

6. The ECG monitoring system according to claim 1, characterized in that, within the hardware, ECG electronic data is stored on a non-volatile memory, the non-volatile memory being configured to record the ECG electronic data for later transmission, and a circuit U8 is composed by a solid-state relay configured for an electromagnetic triggering that releases the medicines in the airtight container, wherein a circuit U7, composed by a solid-state transient-voltage-suppression (TVS) protection circuit, provides protection to the circuit U8 against outbreaks and electrostatic discharges.

7. The ECG monitoring system, according to claim 1, characterized in that the mini-ECG apparatus acquires the ECG electrical signals at a rate of 256 points per second, and the mini-ECG apparatus functions as a 12-lead ECG, wherein the mini ECG apparatus reads a variation of an electrical potential generated by electrical activity in a heart through 8 channels to derive the 12-lead ECG, the ECG electrical signals acquisition occurs for a period of time of at most 24 hours, and the electrodes require 8 seconds to set impedance for each type of skin.

8. The ECG monitoring system according to claim 1 characterized in that the software integrated on the smartphone is further configured to:

add a timestamp to acquired GPS data and the ECG electrical signals and to submit a file data to an FTP server, i) in the case of unsuccessful transmission of the file data, an error log is stored in the software integrated on the smartphone and a new attempt is made until the file data is successfully submitted to the FTP server, ii) the file data is received by the IMS within the datacenter, and in addition, be able to exhibit both recorded ECG electrical signals and real time monitored ECG electrical signals of cardiac signals.

9. The ECG monitoring system according to claim 1, characterized in that the hardware is powered by a rechargeable LI-ION battery and the hardware contains LEDs and a buzzer to provide feedback to the user regarding a stage of an exam process and a battery status.

10. The ECG monitoring system according to claim 1, characterized in that the electrodes may be directly fixed over a skin of the user.

* * * * *